US00PP14489P29

(12) United States Plant Patent
Oliver

(10) Patent No.: US PP14,489 P2
(45) Date of Patent: Jan. 27, 2004

(54) HEUCHERELLA PLANT NAMED 'HEART OF DARKNESS'

(50) Latin Name: ×*Heucherella alba*
Varietal Denomination: Heart of Darkness

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 10/324,931

(22) Filed: Dec. 20, 2002

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Heucherella plant named 'Heart of Darkness', characterized by its full, densely foliated and uniformly mounded plant habit; upper surfaces of leaves green, grayed green and grayed purple in color; lower leaf surfaces green underlain with dark purple in color; numerous large and showy white-colored flowers arranged on erect to outwardly spreading panicles; long flowering period extending from late spring to mid-summer; and excellent garden performance.

2 Drawing Sheets

Botanical classification/cultivar designation: ×*Heucherella alba* cultivar Heart of Darkness.

BACKGROUND OF THE INVENTION

The present invention relates to a new and distinct cultivar of Heucherella plant, botanically known as ×*Heucherella alba* and hereinafter referred to by the name 'Heart of Darkness'. Heucherella is a genus that contains intergeneric hybrids between the genera Heuchera and Tiarella.

The new Heucherella is a product of a planned breeding program conducted by the Inventor in Scottdale, Pa. The objective of the breeding program is to create new Heucherella cultivars having good plant vigor, dense and uniform plant habit, and showy and attractive flower and leaf coloration.

The new Heucherella was discovered by the Inventor in a controlled environment in Scottdale, Pa., from seedling progeny from a cross-pollination made by the Inventor in May, 1999, of the Heuchera cultivar Silver Light, disclosed in U.S. Plant Patent application filed concurrently with this application, as the female, or seed, parent with an unknown selection of *Tiarella cordifolia*, not patented, as the male, or pollen, parent. The new Heucherella was selected by the Inventor in May, 2000. The selection of this plant was based on its desirable flower and foliage coloration.

Asexual reproduction of the new Heucherella by cuttings taken in a controlled environment in Scottdale, Pa., since August, 2000, has shown that the unique features of this new Heucherella are stable and reproduced true to type in successive generations.

SUMMARY OF THE INVENTION

The cultivar Heart of Darkness has not been observed under all possible environmental conditions. The phenotype may vary somewhat with variations in environment such as temperature and light intensity, without, however, any variance in genotype.

The following traits have been repeatedly observed and are determined to be the unique characteristics of 'Heart of Darkness'. These characteristics in combination distinguish 'Heart of Darkness' as a new and distinct cultivar of Heucherella:

1. Full, densely foliated and uniformly mounded plant habit.
2. Upper surfaces of leaves green, grayed green and grayed purple in color; lower leaf surfaces green underlain with dark purple in color.
3. Numerous large and showy white-colored flowers arranged on erect to outwardly spreading panicles.
4. Long flowering period extending from late spring to mid-summer.
5. Excellent garden performance.

Plants of the new Heucherella can be compared to plants of the female parent, the cultivar Silver Light. In side-by-side comparisons conducted by the Inventor in Scottdale, Pa., plants of the new Heucherella differed from plants of the cultivar Silver Light in the following characteristics:

1. Leaves of plants of the new Heucherella had green, grayed green and grayed purple-colored upper leaf surfaces whereas leaves of plants of the cultivar Silver Light had silvery purple-colored upper surfaces.
2. Plants of the new Heucherella had broader inflorescences than plants of the cultivar Silver Light.
3. Flowers of plants of the new Heucherella were white in color whereas flowers of plants of the cultivar Silver Light were pink in color.

Plants of the new Heucherella can be compared to plants of the cultivar Quicksilver, disclosed in U.S. Plant Pat. No. 11,081. In side-by-side comparisons conducted by the Inventor in Scottdale, Pa., plants of the new Heucherella differed from plants of the cultivar Quicksilver in the following characteristics:

1. Leaves of plants of the new Heucherella had green, grayed green and grayed purple-colored upper surfaces whereas leaves of plants of the cultivar Quicksilver had grayed purple to grayed green-colored upper surfaces.

2. Inflorescences of plants of the new Heucherella were shorter and more branched than inflorescences of plants of the cultivar Quicksilver.
3. Flowers of plants of the new Heucherella were larger than flowers of plants of the cultivar Quicksilver.
4. Flowers of plants of the new Heucherella were white in color whereas flowers of plants of the cultivar Quicksilver were light pink in color.

Plants of the new Heucherella can also be compared to plants of the cultivar Kimono, disclosed in U.S. Plant Pat. No. 12,154. In side-by-side comparisons conducted by the Inventor in Scottdale, Pa., plants of the new Heucherella differed from plants of the cultivar Kimono in the following characteristics:

1. Leaves of plants of the new Heucherella were smaller and not as deeply lobed as leaves of plants of the cultivar Kimono.
2. Leaves of plants of the new Heucherella had green, grayed green and grayed purple-colored upper surfaces whereas leaves of plants of the cultivar Kimono had grayed green-colored upper surfaces.
3. Flowers of plants of the new Heucherella were white in color whereas flowers of plants of the cultivar Kimono were greenish white in color.

BRIEF DESCRIPTION OF THE PHOTOGRAPHS

The accompanying colored photographs illustrate the overall appearance of the new Heucherella, showing the colors as true as it is reasonably possible to obtain in colored reproductions of this type. Colors in the photographs may differ slightly from the color values cited in the detailed botanical description which accurately describe the colors of the new Heucherella.

The photograph on the first sheet comprises a side perspective view of a typical one-year old flowering plant of 'Heart of Darkness'.

The photograph on the second sheet is a close-up view of typical inflorescences of 'Heart of Darkness'.

DETAILED BOTANICAL DESCRIPTION

In the following description, color references are made to The Royal Horticultural Society Colour Chart, 1995 Edition, except where general terms of ordinary dictionary significance are used. The following detailed botanical description describes plants grown in Scottdale, Pa. during the summer in a glass-covered greenhouse and under cultural conditions which approximate commercial practice. Plants were grown as single plants in one-gallon containers and were about one year old. During the production of the plants, day temperatures ranged from 15 to 26° C. and night temperatures ranged from 5 to 15° C.

Botanical classification: ×*Heucherella alba* cultivar Heart of Darkness.

Parentage:

*Female, or seed, parent.*—Heuchera sp. cultivar Silver Light, disclosed in U.S. Plant patent application Ser. No. 10/324,932 with this application.

*Male, or pollen, parent.*—Unidentified selection of *Tiarella cordifolia*, not patented.

Propagation:

*Type.*—By cuttings.

*Time to initiate roots.*—Summer: About 15 days at 23° C. Winter: About 21 days at 17° C.

*Time to produce a rooted cutting.*—Summer: About 45 days at 23° C. Winter: About 60 days at 17° C.

*Root description.*—Fine, fibrous and white in color.

*Rooting habit.*—Freely branching.

Plant description:

*Appearance.*—Perennial; basal rosette plant habit with leaves developing from the base; densely foliated; full, mounded and uniform plant habit with upright to outwardly spreading panicles with pink-colored flowers. Vigorous and robust growth habit.

*Plant size.*—Height, soil level to top of foliar plane: About 15 cm. Height, soil level to top of panicles: About 50 cm. Diameter or spread: About 25 to 30 cm.

*Foliage description.*—Arrangement: Basal rosette, simple. Length: About 5 to 8 cm. Width: About 5.5 to 9 cm. Shape: Cordate, rounded; seven-lobed. Apex: Broadly obtuse. Base: Cordate. Margin: Crenate with fine ciliation. Texture, upper and lower surfaces: Slightly pubescent; slightly rough. Venation pattern: Palmate, reticulate. Color: Developing leaves, upper surface: Towards margins, 144C; interveinal 193D; along the veins, 183B. Developing leaves, lower surface: 144C, underlain with 183B along the veins. Fully expanded leaves, upper surface: Towards margins, 143B; interveinal 193D; along the veins, 183B. Fully expanded leaves, lower surface: 143C, underlain with 183B along the veins. Venation, upper surface: 143B. Venation, lower surface: 143C. Petiole: Length: About 5 to 9 cm. Diameter: About 1 to 1.5 mm. Texture, upper and lower surfaces: Pubescent. Color, upper and lower surfaces: 186D underlain with 143B.

Flower description:

*Appearance/arrangement.*—Single campanulate flowers arranged on numerous erect to outwardly spreading panicles; about 50 to 100 flowers and flower buds per flowering stem. Flowers face outward to slightly upright. Flowering continuous. Flowers persistent. Flowers not fragrant.

*Time of flowering.*—Long flowering period, plants flower from May to July in Scottdale, Pa.

*Inflorescence longevity.*—Individual inflorescences last about one week on the plant.

*Inflorescence size.*—Length: About 30 to 50 cm. Diameter: About 15 to 20 cm.

*Flower size.*—Diameter: About 1.3 mm. Depth (height): About 6 mm.

*Flower buds.*—Height: About 3 mm. Diameter: About 2.5 mm. Shape: Bulbous. Color, at stage of showing color: 157C.

*Sepals.*—*Quantity/arrangement: Five sepals; radially symmetrical and fused at base. Calyx length: About* 4 mm. Calyx diameter: About 4 mm. Shape: Elongate. Apex: Obtuse. Margin: Entire. Texture, upper and lower surfaces: Pubescent. Color, when opening and fully opened, upper and lower surfaces: Close to 155D.

*Petals.*—Quantity/arrangement: Five minute petals; radially symmetrical. Length: About 3 to 5 mm. Width: About 1 mm. Shape: Ellipsoid. Apex: Acute. Margin: Entire. Texture, upper and lower surfaces: Slightly pubescent. Color, when opening and fully opened, upper and lower surfaces: Close to 155D.

*Flower bracts.*—Length: About 1.5 to 2 mm. Width: About 0.1 to 0.2 mm. Shape: Lanceolate. Apex:

Acute. Margin: Deeply serrate. Texture, upper and lower surfaces: Slightly pubescent. Color, upper and lower surfaces: 143B.

*Peduncle.*—Strength: Strong. Aspect: Upright to angled outwardly to 30° from vertical. Length: About 20 to 30 cm. Diameter: About 1.5 to 2 mm. Texture: Smooth. Color: 186D underlain with 143B.

*Pedicels.*—Strength: Strong. Aspect: About 60° from vertical. Length: About 3 mm. Diameter: About 0.3 mm. Texture: Pubescent. Color: 143B.

*Reproductive organs.*—Androecium: Stamen number: Five per flower. Anther shape: Bi-lobed. Anther size: About 0.2 mm by 0.6 mm. Anther color: 22A. Amount of pollen: None observed. Gynoecium: Pistil number: Two per flower. Pistil length: About 5 mm. Stigma shape: Round. Stigma color: 157C. Style length: About 3.5 mm. Style color: 157C. Ovary color: 157C.

*Seed.*—Seed production has not been observed.

Disease/pest resistance: Resistance to pathogens and pests common to Heucherella has not been observed on plants grown under commercial conditions.

Weather/temperature tolerance: Plants of the new Heucherella have been observed to have excellent garden performance. Plants of the new Heucherella have demonstrated good tolerance to rain, wind, night temperatures as low as −35° C., and day temperatures as high as 45° C.

It is claimed:

1. A new and distinct cultivar of Heucherella plant named 'Heart of Darkness', as illustrated and described.

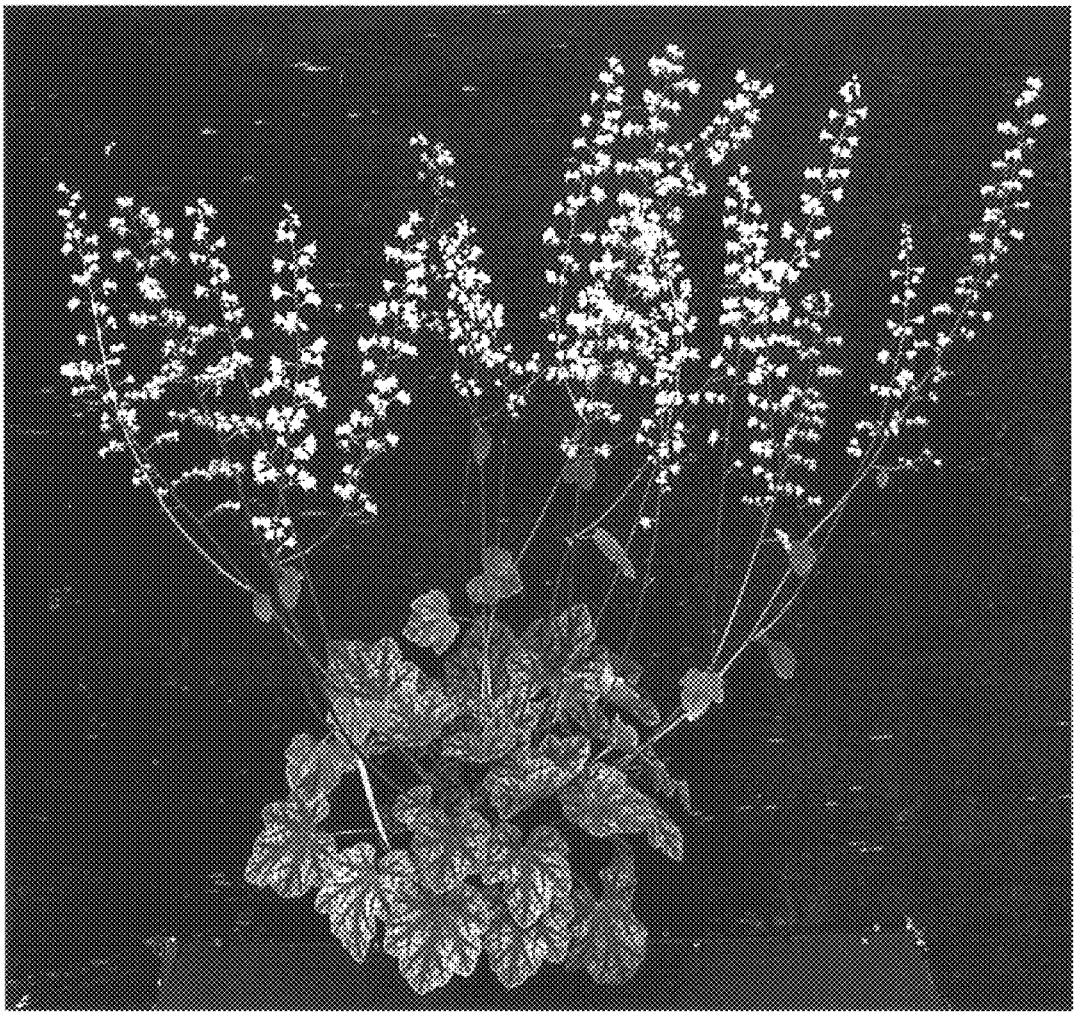

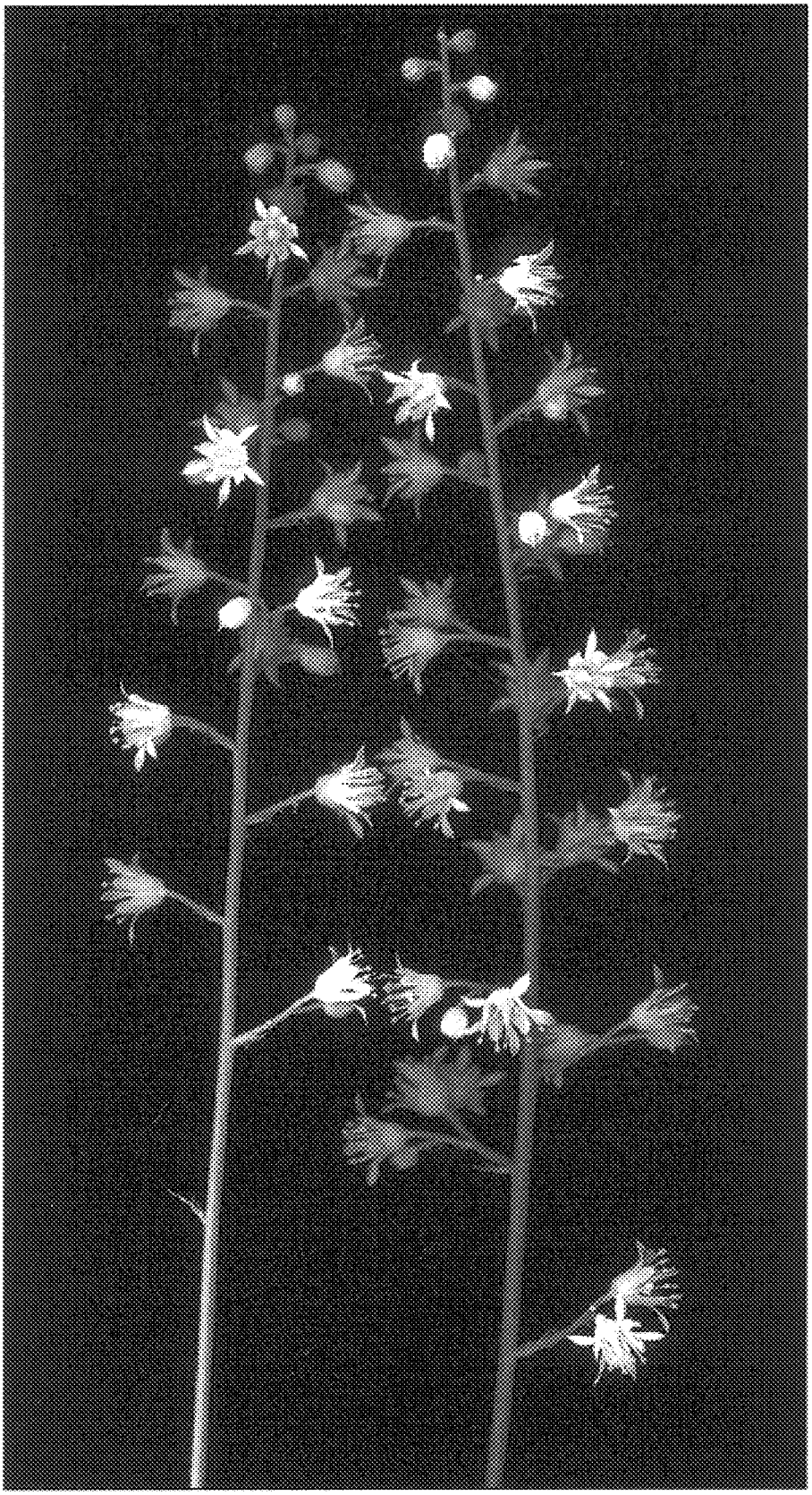

* * * * *